(12) United States Patent
Beeckler et al.

(10) Patent No.: US 11,987,017 B2
(45) Date of Patent: May 21, 2024

(54) FEATURES TO ASSIST IN ASSEMBLY AND TESTING OF DEVICES

(71) Applicant: Biosense Webster (Israel) Ltd., Yokneam (IL)

(72) Inventors: Christopher Thomas Beeckler, Brea, CA (US); Zulema Berenice Espinoza, Moreno Valley, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 885 days.

(21) Appl. No.: 16/896,104

(22) Filed: Jun. 8, 2020

(65) Prior Publication Data
US 2021/0378594 A1     Dec. 9, 2021

(51) Int. Cl.
*B29D 23/00*     (2006.01)
*A61B 5/00*      (2006.01)
(Continued)

(52) U.S. Cl.
CPC .............. *B29D 23/00* (2013.01); *A61B 5/062* (2013.01); *A61B 5/6858* (2013.01); *A61M 25/001* (2013.01); *A61M 39/10* (2013.01); *G01R 31/54* (2020.01); *A61B 2560/0223* (2013.01); *A61B 2562/125* (2013.01); *A61M 2039/1022* (2013.01)

(58) Field of Classification Search
CPC ..... B29D 23/00; A61M 25/001; A61M 39/10; A61M 2039/1022; A61B 5/062; A61B 5/6858; A61B 2560/0223; A61B 2562/125; A61B 90/94; A61B 2018/00267; A61B 2090/0808; A61B 2017/00526; A61B 18/1492; A61B 18/00; A61B 18/14; G01R 31/54; A61N 1/05
See application file for complete search history.

(56) References Cited

U.S. PATENT DOCUMENTS

| 4,699,147 A | 10/1987 | Chilson et al. |
| 4,857,857 A * | 8/1989 | Valenti ............... G01R 31/52 324/555 |

(Continued)

FOREIGN PATENT DOCUMENTS

| CA | 3107959 A1 * | 2/2020 | ......... A61B 18/1492 |
| CN | 111248993 A | 6/2020 | |

(Continued)

OTHER PUBLICATIONS

Extended European Search Report dated Nov. 5, 2021, from corresponding EP Application No. 21178056.4.

*Primary Examiner* — Jeffrey T Carley
(74) *Attorney, Agent, or Firm* — Troutman Pepper Hamilton Sanders LLP

(57) ABSTRACT

In one embodiment, a catheter manufacturing method includes forming flexible circuit strips with respective different symbols marked thereon, each strip including at least one respective electrode, attaching one end of each of the flexible circuit strips to a catheter coupler with the flexible circuit strips being ordered around a circumference of the catheter coupler responsively to the respective symbols of respective ones of the flexible circuit strips, and forming a distal end assembly of a catheter, the distal end assembly comprising the flexible circuit strips attached to the catheter coupler.

15 Claims, 9 Drawing Sheets

(51) Int. Cl.
*A61B 5/06* (2006.01)
*A61M 25/00* (2006.01)
*A61M 39/10* (2006.01)
*G01R 31/54* (2020.01)

(56) References Cited

U.S. PATENT DOCUMENTS

| | | | |
|---|---|---|---|
| 4,940,064 A | 7/1990 | Desai | |
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A * | 5/1997 | Webster, Jr. | A61B 5/6858 600/374 |
| 5,681,280 A | 10/1997 | Rusk et al. | |
| 5,722,401 A * | 3/1998 | Pietroski | A61B 5/6858 600/374 |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,581 A * | 1/2000 | Whayne | A61B 5/6858 600/523 |
| 6,014,590 A | 1/2000 | Whayne et al. | |
| 6,050,267 A * | 4/2000 | Nardella | A61B 5/063 128/899 |
| 6,115,626 A * | 9/2000 | Whayne | A61B 5/287 600/523 |
| 6,119,030 A | 9/2000 | Morency | |
| 6,216,043 B1 | 4/2001 | Swanson et al. | |
| 6,216,044 B1 | 4/2001 | Kordis | |
| 6,239,724 B1 | 5/2001 | Doron et al. | |
| 6,332,089 B1 * | 12/2001 | Acker | A61N 7/02 128/899 |
| 6,428,537 B1 | 8/2002 | Swanson et al. | |
| 6,456,864 B1 | 9/2002 | Swanson et al. | |
| 6,484,118 B1 * | 11/2002 | Govari | A61B 34/20 702/94 |
| 6,574,492 B1 * | 6/2003 | Ben-Haim | A61B 5/287 600/374 |
| 6,584,345 B2 | 6/2003 | Govari | |
| 6,600,948 B2 | 7/2003 | Ben-Haim et al. | |
| 6,618,612 B1 * | 9/2003 | Acker | A61B 90/36 128/899 |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,944,490 B1 * | 9/2005 | Chow | A61B 5/283 600/374 |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 7,974,674 B2 * | 7/2011 | Hauck | A61B 34/20 607/9 |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,155,910 B2 * | 4/2012 | Hauck | A61B 1/0052 600/407 |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 * | 3/2017 | Marecki | A61B 5/287 |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |

(56) References Cited

U.S. PATENT DOCUMENTS

| | | | |
|---|---|---|---|
| 10,136,828 B2 | 11/2018 | Houben et al. |
| 10,143,394 B2 | 12/2018 | Solis |
| 10,172,536 B2 | 1/2019 | Maskara et al. |
| 10,182,762 B2 | 1/2019 | Just et al. |
| 10,194,818 B2 | 2/2019 | Williams et al. |
| 10,201,311 B2 | 2/2019 | Chou et al. |
| 10,219,860 B2 | 3/2019 | Harlev et al. |
| 10,219,861 B2 | 3/2019 | Just et al. |
| 10,231,328 B2 | 3/2019 | Weinkam et al. |
| 10,238,309 B2 | 3/2019 | Bar-Tal et al. |
| 10,278,590 B2 | 5/2019 | Salvestro et al. |
| D851,774 S | 6/2019 | Werneth et al. |
| 10,314,505 B2 | 6/2019 | Williams et al. |
| 10,314,507 B2 | 6/2019 | Govari et al. |
| 10,314,648 B2 | 6/2019 | Ge et al. |
| 10,314,649 B2 | 6/2019 | Bakos et al. |
| 10,349,855 B2 | 7/2019 | Zeidan et al. |
| 10,350,003 B2 | 7/2019 | Weinkam et al. |
| 10,362,991 B2 | 7/2019 | Tran et al. |
| 10,375,827 B2 | 8/2019 | Weinkam et al. |
| 10,376,170 B2 | 8/2019 | Quinn et al. |
| 10,376,221 B2 | 8/2019 | Iyun et al. |
| 10,398,348 B2 | 9/2019 | Osadchy et al. |
| 10,403,053 B2 | 9/2019 | Katz et al. |
| 10,441,188 B2 | 10/2019 | Katz et al. |
| 10,470,682 B2 | 11/2019 | Deno et al. |
| 10,470,714 B2 | 11/2019 | Altmann et al. |
| 10,482,198 B2 | 11/2019 | Auerbach et al. |
| 10,492,857 B2 | 12/2019 | Guggenberger et al. |
| 10,542,620 B2 | 1/2020 | Weinkam et al. |
| 10,575,743 B2 | 3/2020 | Basu et al. |
| 10,575,745 B2 | 3/2020 | Solis |
| 10,582,871 B2 | 3/2020 | Williams et al. |
| 10,582,894 B2 | 3/2020 | Ben Zrihem et al. |
| 10,596,346 B2 | 3/2020 | Aeby et al. |
| 10,602,947 B2 | 3/2020 | Govari et al. |
| 10,617,867 B2 | 4/2020 | Viswanathan et al. |
| 10,660,702 B2 | 5/2020 | Viswanathan et al. |
| 10,667,753 B2 | 6/2020 | Werneth et al. |
| 10,674,929 B2 | 6/2020 | Houben et al. |
| 10,681,805 B2 | 6/2020 | Weinkam et al. |
| 10,682,181 B2 | 6/2020 | Cohen et al. |
| 10,687,892 B2 | 6/2020 | Long et al. |
| 10,702,178 B2 | 7/2020 | Dahlen et al. |
| 10,716,477 B2 | 7/2020 | Salvestro et al. |
| 10,758,304 B2 | 9/2020 | Aujla |
| 10,765,371 B2 | 9/2020 | Hayam et al. |
| 10,772,566 B2 | 9/2020 | Aujila |
| 10,799,281 B2 | 10/2020 | Goertzen et al. |
| 10,842,558 B2 | 11/2020 | Harlev et al. |
| 10,842,561 B2 | 11/2020 | Viswanathan et al. |
| 10,863,914 B2 | 12/2020 | Govari et al. |
| 10,881,376 B2 | 1/2021 | Shemesh et al. |
| 10,898,139 B2 | 1/2021 | Guta et al. |
| 10,905,329 B2 | 2/2021 | Bar-Tal et al. |
| 10,912,484 B2 | 2/2021 | Ziv-Ari et al. |
| 10,918,306 B2 | 2/2021 | Govari et al. |
| 10,939,871 B2 | 3/2021 | Altmann et al. |
| 10,952,795 B2 | 3/2021 | Cohen et al. |
| 10,973,426 B2 | 4/2021 | Williams et al. |
| 10,973,461 B2 | 4/2021 | Baram et al. |
| 10,987,045 B2 | 4/2021 | Basu et al. |
| 11,006,902 B1 | 5/2021 | Bonyak et al. |
| 11,040,208 B1 | 6/2021 | Govari et al. |
| 11,045,628 B2 | 6/2021 | Beeckler et al. |
| 11,051,877 B2 | 7/2021 | Sliwa et al. |
| 11,077,298 B2* | 8/2021 | Waldhauser ......... A61N 1/0551 |
| 11,109,788 B2 | 9/2021 | Rottmann et al. |
| 11,116,435 B2 | 9/2021 | Urman et al. |
| 11,129,574 B2 | 9/2021 | Cohen et al. |
| 11,160,482 B2 | 11/2021 | Solis |
| 11,164,371 B2 | 11/2021 | Yellin et al. |
| 2002/0006455 A1 | 1/2002 | Levine |
| 2002/0032380 A1 | 3/2002 | Acker et al. |
| 2003/0120150 A1 | 6/2003 | Govari |
| 2004/0068178 A1 | 4/2004 | Govari |
| 2004/0210121 A1 | 10/2004 | Fuimaono et al. |
| 2006/0009689 A1 | 1/2006 | Fuimaono et al. |
| 2006/0009690 A1 | 1/2006 | Fuimaono et al. |
| 2006/0100669 A1 | 5/2006 | Fuimaono et al. |
| 2007/0093806 A1 | 4/2007 | Desai et al. |
| 2007/0276212 A1 | 11/2007 | Fuimaono et al. |
| 2008/0234564 A1 | 9/2008 | Beatty et al. |
| 2008/0252311 A1 | 10/2008 | Koh et al. |
| 2009/0253976 A1* | 10/2009 | Harlev ............... A61B 5/0538 606/41 |
| 2011/0118726 A1 | 5/2011 | De La Rama et al. |
| 2011/0160574 A1 | 6/2011 | Harlev et al. |
| 2011/0190625 A1 | 8/2011 | Harlev et al. |
| 2011/0245756 A1 | 10/2011 | Arora et al. |
| 2011/0301597 A1 | 12/2011 | McDaniel et al. |
| 2013/0172872 A1 | 7/2013 | Subramaniam et al. |
| 2013/0172883 A1 | 7/2013 | Lopes et al. |
| 2013/0178850 A1 | 7/2013 | Lopes et al. |
| 2013/0190587 A1 | 7/2013 | Lopes et al. |
| 2013/0289369 A1 | 10/2013 | Margolis |
| 2013/0296852 A1 | 11/2013 | Madjarov et al. |
| 2014/0025069 A1 | 1/2014 | Willard et al. |
| 2014/0052118 A1 | 2/2014 | Laske et al. |
| 2014/0180147 A1 | 6/2014 | Thakur et al. |
| 2014/0180151 A1 | 6/2014 | Maskara et al. |
| 2014/0180152 A1 | 6/2014 | Maskara et al. |
| 2014/0257069 A1 | 9/2014 | Eliason et al. |
| 2014/0276712 A1 | 9/2014 | Mallin et al. |
| 2014/0309512 A1 | 10/2014 | Govari et al. |
| 2014/0350655 A1* | 11/2014 | North ............... A61N 1/0558 607/117 |
| 2015/0011991 A1 | 1/2015 | Buysman et al. |
| 2015/0045863 A1 | 2/2015 | Litscher et al. |
| 2015/0080693 A1 | 3/2015 | Solis |
| 2015/0105770 A1 | 4/2015 | Amit |
| 2015/0119878 A1 | 4/2015 | Heisel et al. |
| 2015/0133919 A1 | 5/2015 | McDaniel et al. |
| 2015/0173183 A1 | 6/2015 | Holec et al. |
| 2015/0208942 A1 | 7/2015 | Bar-Tal et al. |
| 2015/0250424 A1 | 9/2015 | Govari et al. |
| 2015/0270634 A1 | 9/2015 | Buesseler et al. |
| 2015/0342532 A1 | 12/2015 | Basu et al. |
| 2016/0081746 A1 | 3/2016 | Solis |
| 2016/0113582 A1 | 4/2016 | Altmann et al. |
| 2016/0113709 A1 | 4/2016 | Maor |
| 2016/0183877 A1 | 6/2016 | Williams et al. |
| 2016/0228023 A1 | 8/2016 | Govari |
| 2016/0228062 A1 | 8/2016 | Altmann et al. |
| 2016/0278853 A1 | 9/2016 | Ogle et al. |
| 2016/0302858 A1 | 10/2016 | Bencini |
| 2016/0338770 A1 | 11/2016 | Bar-Tal et al. |
| 2017/0027638 A1 | 2/2017 | Solis |
| 2017/0055346 A1 | 2/2017 | Holec et al. |
| 2017/0065227 A1 | 3/2017 | Marrs et al. |
| 2017/0071543 A1 | 3/2017 | Basu et al. |
| 2017/0071544 A1 | 3/2017 | Basu et al. |
| 2017/0071665 A1 | 3/2017 | Solis |
| 2017/0095173 A1 | 4/2017 | Bar-Tal et al. |
| 2017/0100187 A1 | 4/2017 | Basu et al. |
| 2017/0143227 A1 | 5/2017 | Marecki et al. |
| 2017/0156790 A1 | 6/2017 | Aujla |
| 2017/0172442 A1 | 6/2017 | Govari |
| 2017/0185702 A1 | 6/2017 | Auerbach et al. |
| 2017/0202515 A1 | 7/2017 | Zrihem et al. |
| 2017/0221262 A1 | 8/2017 | Laughner et al. |
| 2017/0224958 A1* | 8/2017 | Cummings ......... A61B 5/6858 |
| 2017/0265812 A1 | 9/2017 | Williams et al. |
| 2017/0281031 A1 | 10/2017 | Houben et al. |
| 2017/0281268 A1 | 10/2017 | Tran et al. |
| 2017/0296125 A1 | 10/2017 | Altmann et al. |
| 2017/0296251 A1 | 10/2017 | Wu et al. |
| 2017/0347959 A1 | 12/2017 | Guta et al. |
| 2017/0354338 A1 | 12/2017 | Levin et al. |
| 2017/0354339 A1 | 12/2017 | Zeidan et al. |
| 2017/0354364 A1 | 12/2017 | Bar-Tal et al. |
| 2018/0008203 A1 | 1/2018 | Iyun et al. |
| 2018/0028084 A1 | 2/2018 | Williams et al. |
| 2018/0049803 A1 | 2/2018 | Solis |

(56) References Cited

U.S. PATENT DOCUMENTS

| | | |
|---|---|---|
| 2018/0085064 A1 | 3/2018 | Auerbach et al. |
| 2018/0132749 A1 | 5/2018 | Govari et al. |
| 2018/0137687 A1 | 5/2018 | Katz et al. |
| 2018/0160936 A1 | 6/2018 | Govari et al. |
| 2018/0160978 A1 | 6/2018 | Cohen et al. |
| 2018/0168503 A1* | 6/2018 | Waldhauser ............ A61B 5/287 |
| 2018/0168511 A1 | 6/2018 | Hall et al. |
| 2018/0184982 A1 | 7/2018 | Basu et al. |
| 2018/0192958 A1 | 7/2018 | Wu |
| 2018/0206792 A1 | 7/2018 | Auerbach et al. |
| 2018/0235692 A1 | 8/2018 | Efimov et al. |
| 2018/0249959 A1 | 9/2018 | Osypka |
| 2018/0256109 A1 | 9/2018 | Wu et al. |
| 2018/0279954 A1 | 10/2018 | Hayam et al. |
| 2018/0303414 A1 | 10/2018 | Toth et al. |
| 2018/0310987 A1 | 11/2018 | Altmann et al. |
| 2018/0311497 A1 | 11/2018 | Viswanathan et al. |
| 2018/0338722 A1 | 11/2018 | Altmann et al. |
| 2018/0344188 A1 | 12/2018 | Govari |
| 2018/0344202 A1* | 12/2018 | Bar-Tal .................. A61B 17/00 |
| 2018/0344251 A1 | 12/2018 | Harlev et al. |
| 2018/0344393 A1 | 12/2018 | Gruba et al. |
| 2018/0360534 A1 | 12/2018 | Teplitsky et al. |
| 2018/0365355 A1 | 12/2018 | Auerbach et al. |
| 2019/0000540 A1 | 1/2019 | Cohen et al. |
| 2019/0008582 A1 | 1/2019 | Govari et al. |
| 2019/0015007 A1 | 1/2019 | Rottmann et al. |
| 2019/0030328 A1 | 1/2019 | Stewart et al. |
| 2019/0053708 A1 | 2/2019 | Gliner |
| 2019/0059766 A1 | 2/2019 | Houben et al. |
| 2019/0059819 A1 | 2/2019 | Jung et al. |
| 2019/0069950 A1 | 3/2019 | Viswanathan et al. |
| 2019/0069954 A1 | 3/2019 | Cohen et al. |
| 2019/0117111 A1 | 4/2019 | Osadchy et al. |
| 2019/0117303 A1 | 4/2019 | Claude et al. |
| 2019/0117315 A1 | 4/2019 | Keyes et al. |
| 2019/0125439 A1 | 5/2019 | Rohl et al. |
| 2019/0133552 A1 | 5/2019 | Shemesh et al. |
| 2019/0142293 A1 | 5/2019 | Solis |
| 2019/0164633 A1 | 5/2019 | Ingel et al. |
| 2019/0167137 A1 | 6/2019 | Bar-Tal et al. |
| 2019/0167140 A1 | 6/2019 | Williams et al. |
| 2019/0188909 A1 | 6/2019 | Yellin et al. |
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | DeSimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0169421 A1 | 6/2021 | Govari |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0178166 A1 | 6/2021 | Govari et al. |
| 2021/0186363 A1 | 6/2021 | Gliner et al. |
| 2021/0187241 A1 | 6/2021 | Govari et al. |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | | |
|---|---|---|---|
| CN | 111248996 A | 6/2020 | |
| EP | 0668740 A1 | 8/1995 | |
| EP | 0644738 B1 | 3/2000 | |
| EP | 0727183 B1 | 11/2002 | |
| EP | 0727184 B1 | 12/2002 | |
| EP | 0932362 B1 | 1/2005 | |
| EP | 2783651 A1 | 10/2014 | |
| EP | 2910186 A1 * | 8/2015 | ......... A61B 18/1492 |
| EP | 2699151 B1 | 11/2015 | |
| EP | 2699152 B1 | 11/2015 | |
| EP | 2699153 B1 | 12/2015 | |
| EP | 2983603 B1 | 2/2016 | |
| EP | 2498706 B1 | 4/2016 | |
| EP | 2578173 B1 | 6/2017 | |
| EP | 3238645 A1 | 11/2017 | |
| EP | 2884931 B1 | 1/2018 | |
| EP | 2349440 B1 | 8/2019 | |
| EP | 3318211 B1 | 12/2019 | |
| EP | 3581135 A1 | 12/2019 | |
| EP | 2736434 B1 | 2/2020 | |
| EP | 3451962 B1 | 3/2020 | |
| EP | 3972510 A1 | 3/2022 | |
| WO | 9421167 A1 | 9/1994 | |
| WO | 9421169 A1 | 9/1994 | |
| WO | WO 1996/005768 A1 | 2/1996 | |

(56) References Cited

FOREIGN PATENT DOCUMENTS

| | | | |
|---|---|---|---|
| WO | 9625095 | A1 | 8/1996 |
| WO | 9634560 | A1 | 11/1996 |
| WO | 0182814 | B1 | 5/2002 |
| WO | 2004087249 | A2 | 10/2004 |
| WO | 2012100185 | A2 | 7/2012 |
| WO | 2013052852 | A1 | 4/2013 |
| WO | 2013162884 | A1 | 10/2013 |
| WO | 2013173917 | A1 | 11/2013 |
| WO | 2013176881 | A1 | 11/2013 |
| WO | 2014176205 | A1 | 10/2014 |
| WO | 2016019760 | A1 | 2/2016 |
| WO | 2016044687 | A1 | 3/2016 |
| WO | WO-2016030178 | A1 * | 3/2016 ............... A61B 1/04 |
| WO | 2018111600 | A1 | 6/2018 |
| WO | 2018191149 | A1 | 10/2018 |
| WO | WO-2018222101 | A1 * | 12/2018 ............... A61B 5/24 |
| WO | 2019084442 | A1 | 5/2019 |
| WO | 2019143960 | A1 | 7/2019 |
| WO | 2020026217 | A1 | 2/2020 |
| WO | 2020206328 | A1 | 10/2020 |

\* cited by examiner

FEATURES TO ASSIST IN ASSEMBLY AND TESTING OF DEVICES

FIELD OF THE INVENTION

The present invention relates to medical devices, and in particular, but not exclusively to, catheter devices.

BACKGROUND

A wide range of medical procedures involve placing probes, such as catheters, within a patient's body. Location sensing systems have been developed for tracking such probes. Magnetic location sensing is one of the methods known in the art. In magnetic location sensing, magnetic field generators are typically placed at known locations external to the patient. A magnetic field sensor within the distal end of the probe generates electrical signals in response to these magnetic fields, which are processed to determine the coordinate locations of the distal end of the probe. These methods and systems are described in U.S. Pat. Nos. 5,391,199, 6,690,963, 6,484,118, 6,239,724, 6,618,612 and 6,332,089, in PCT International Publication No. WO 1996/005768, and in U.S. Patent Application Publications Nos. 2002/006455 and 2003/0120150 and 2004/0068178. Locations may also be tracked using impedance or current based systems.

One medical procedure in which these types of probes or catheters have proved extremely useful is in the treatment of cardiac arrhythmias. Cardiac arrhythmias and atrial fibrillation in particular, persist as common and dangerous medical ailments, especially in the aging population.

Diagnosis and treatment of cardiac arrhythmias include mapping the electrical properties of heart tissue, especially the endocardium, and selectively ablating cardiac tissue by application of energy. Such ablation can cease or modify the propagation of unwanted electrical signals from one portion of the heart to another. The ablation process destroys the unwanted electrical pathways by formation of non-conducting lesions. Various energy delivery modalities have been disclosed for forming lesions, and include use of microwave, laser and more commonly, radiofrequency energies to create conduction blocks along the cardiac tissue wall. In a two-step procedure, mapping followed by ablation, electrical activity at points within the heart is typically sensed and measured by advancing a catheter containing one or more electrical sensors into the heart, and acquiring data at a multiplicity of points. These data are then utilized to select the endocardial target areas at which the ablation is to be performed.

Electrode catheters have been in common use in medical practice for many years. They are used to stimulate and map electrical activity in the heart and to ablate sites of aberrant electrical activity. In use, the electrode catheter is inserted into a major vein or artery, e.g., femoral vein, and then guided into the chamber of the heart of concern. A typical ablation procedure involves the insertion of a catheter having a one or more electrodes at its distal end into a heart chamber. A reference electrode may be provided, generally taped to the skin of the patient or by means of a second catheter that is positioned in or near the heart. RF (radio frequency) current is applied through the tip electrode(s) of the ablating catheter, and current flows through the media that surrounds it, i.e., blood and tissue, between the tip electrode(s) and an indifferent electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive.

US Patent Publication 2008/0252311 of Koh, et al., describes an apparatus and method for performing a verification buy-off operation during an assembly manufacturing process, such as during printed circuit board (PCB) manufacturing. A processing device is configured to establish contact between a probe assembly and a first component of an assembly having a plurality of components loaded in predetermined positions but not yet electrically intercoupled, and to receive from the probe assembly a component value associated with the first component. Preferably, the processing device further determines whether the received component value is within a predetermined specification. The processing device preferably directs a user via a graphical user interface (GUI) to manipulate the probe assembly to a position proximate the first component. The GUI preferably provides a graphical representation of the assembly and a marker that identifies the location of the first component thereon. All of the components of the assembly are preferably verified individually prior to a full production run.

US Patent Publication 2015/0173183 of Holec, et al., describes an interconnectable circuit board which includes one or more of the following features: (a) a first electrically conductive pad located on a top of the circuit board, (b) a plated through hole on the conductive pad which passes through the circuit board, (c) a second electrically conductive pad coupled to the plated through hole; the second conductive pad capable of being electrically connected to a third electrically conductive pad attached to a top of a second interconnectable circuit board, (d) cut marks indicating safe locations for separating the circuit board, and (e) a second cut mark adjacent to the first cut mark where the area between the first and second cut mark can be utilized to make a safe cut through the circuit board.

SUMMARY

There is provided in accordance with an embodiment of the present disclosure, a catheter manufacturing method, including forming flexible circuit strips with respective different symbols marked thereon, each strip including at least one respective electrode, attaching one end of each of the flexible circuit strips to a catheter coupler with the flexible circuit strips being ordered around a circumference of the catheter coupler responsively to the respective symbols of respective ones of the flexible circuit strips, and forming a distal end assembly of a catheter, the distal end assembly including the flexible circuit strips attached to the catheter coupler.

Further in accordance with an embodiment of the present disclosure, the method includes connecting the catheter coupler to an elongated deflectable element.

Still further in accordance with an embodiment of the present disclosure the forming the flexible strips includes forming the flexible circuit strips with respective alignment markings, and the attaching includes aligning the end of each of the flexible circuit strips to the catheter coupler responsively to the respective alignment markings of respective ones of the flexible circuit strips.

Additionally, in accordance with an embodiment of the present disclosure, the method includes forming a flexible circuit panel including the flexible circuit strips in uncut form, and cutting the flexible circuit panel to form the flexible circuit strips as separated strips.

Moreover, in accordance with an embodiment of the present disclosure forming the flexible circuit panel includes forming the flexible circuit panel with multiple copies of each of the symbols.

Further in accordance with an embodiment of the present disclosure, the method includes aligning the distal end assembly with a position tracking system responsively to one of the symbols of a respective one of the flexible circuit strips, and performing a calibration of the catheter with the position tracking system responsively to the aligning.

Still further in accordance with an embodiment of the present disclosure, the method includes aligning a plane of deflection of the distal end assembly with a deflection measurement element responsively to one of the symbols of a respective one of the flexible circuit strips, deflecting the catheter, and checking a deflection of the catheter with the deflection measurement element.

Additionally, in accordance with an embodiment of the present disclosure, the method includes checking a continuity of electrodes of the catheter responsively to respective ones of the symbols of respective ones of the flexible circuit strips.

There is also provided in accordance with another embodiment of the present disclosure, a catheter calibration method, including connecting a catheter with a position tracking system, the catheter including a distal end assembly including flexible circuit strips with respective different symbols marked thereon, each strip including at least one respective electrode, one end of each of the flexible circuit strips being connected to a catheter coupler with the flexible circuit strips being ordered around a circumference of the catheter coupler responsively to the respective symbols of respective ones of the flexible circuit strips, aligning the distal end assembly with the position tracking system responsively to one of the symbols of a respective one of the flexible circuit strips, and performing a calibration of the catheter with the position tracking system responsively to the aligning.

There is also provided in accordance with still another embodiment of the present disclosure, a catheter device, including a distal end assembly including flexible circuit strips with respective different symbols marked thereon, each strip including at least one respective electrode, and a catheter coupler, one end of each of the flexible circuit strips being connected to the catheter coupler with the flexible circuit strips being ordered around a circumference of the catheter coupler responsively to the respective symbols of respective ones of the flexible circuit strips.

Moreover, in accordance with an embodiment of the present disclosure, the device includes an elongated deflectable element connected to the catheter coupler.

BRIEF DESCRIPTION OF THE DRAWINGS

The present invention will be understood from the following detailed description, taken in conjunction with the drawings in which.

DESCRIPTION OF EXAMPLE EMBODIMENTS

Overview

Figure 1:
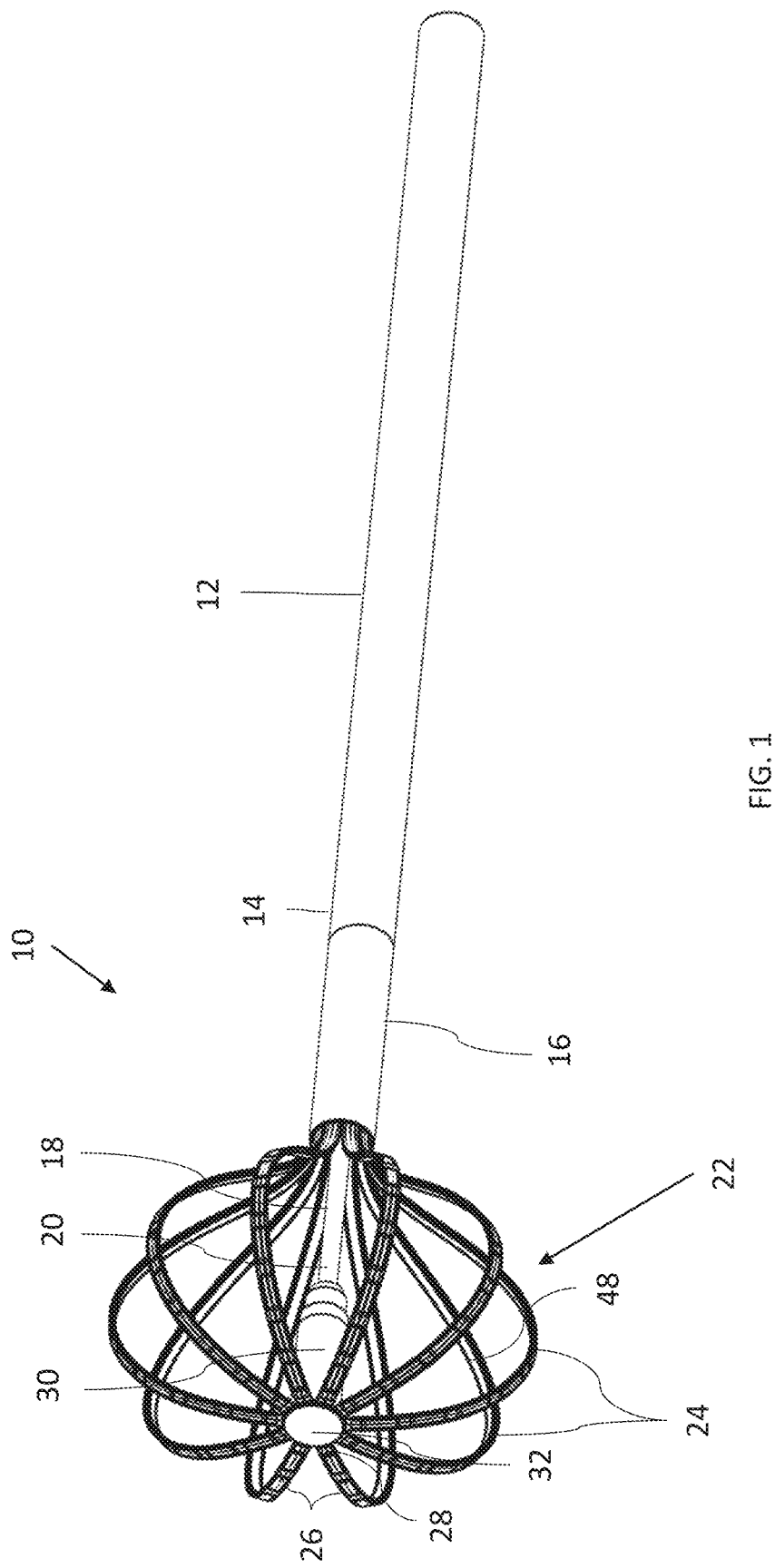
FIG. 1 is a schematic view of a catheter constructed and operative in accordance with an embodiment of the present invention.

When testing catheters such as a basket catheter it is often easy to confuse one spline of the basket with another, especially if the catheter is bidirectional as there is no easy curve indicator to align to. For example, if the catheter has ten or more splines it is often hard to choose which of the two splines is most in plane with the deflection curve in order to test the deflection of the catheter.

During assembly, the electrodes on the splines are checked for continuity and if the testing operator confuses one spline with another, it can create erroneous readings or delays in testing.

One solution to the above problems is to provide additional electrode rings on one or more of the splines to help distinguish one spline from the other. While an additional electrode may be a useful indicator, it only identifies one or two of the splines and requires some interpretation.

Embodiments of the present invention solve the above problems by directly labelling the flexible circuit strips of catheter splines with letters (e.g., A, B, C etc.) or other symbols (e.g., numerals). Any character or shape that is legible can be applied to the circuit. The letters or other symbols may then be used in catheter manufacture to easily determine how the splines should be connected to the rest of the catheter. The letters or other symbols may also be useful during testing and configuration by easily allowing an operator to align the catheter according to the letters or symbols shown on the splines. For example, during configuration, the catheter may be easily aligned to a position tracking system using the letters or other symbols. The letters or symbols may also be useful to identify problems with the catheter or its configuration. The letters or symbols may be easily added to the flexible circuit design along with the functional component of the flexible circuit strips.

Alignment marks (e.g., lines) may also be added to flexible circuit strips to help align parts during manufacture rather than relying upon additional measurements. These alignment marks may also serve as additional post-assembly checks to verify that the device was assembled properly.

It should be noted that the differently labeled strips may also comprise different electrical functionality and/or a different number and/or a different spacing of electrodes. In other embodiments, two or more of the differently labeled strips may be identical apart from the different labeling.

A problem may occur when assembling basket catheters from splines formed from a panel of flexible circuits which includes individual strips. If one of the strips is faulty, the whole set may need to be discarded. Embodiments of the present invention provide a more cost-effective manufacturing process by labelling the flexible circuit strips with letters or symbols and providing duplicate flexible circuit strips on a single panel so that if one strip is faulty, another one with the same letter of symbol may be used instead. For example, 880 circuit strips may be formed on a single flexible circuit panel with the strips being labeled A through J (for example) again and again. The flexible circuit panel is then cut up. If one of the strips (or splines) marked "A" (for example) proves to be faulty, another "A" strip (or spline) may be used instead, and so on.

Embodiments of the present invention include a catheter device including a distal end assembly comprising flexible circuit strips with respective different symbols marked thereon, each strip including at least one respective electrode. The catheter device also includes a catheter coupler. One end of each flexible circuit strip is connected to the catheter coupler with the flexible circuit strips being ordered around a circumference of the catheter coupler responsively to the respective symbols (e.g., in the order A, B, C and so on from some marker) of the flexible circuit strips. In some embodiments an elongated deflectable element is connected proximally to the catheter coupler. In other embodiments the catheter coupler is formed integrally with the elongated deflectable element.

Embodiments of the present invention include a catheter manufacturing method which includes forming a distal end assembly of a catheter from flexible circuit strips attached to a catheter coupler which may be connected proximally to an elongated deflectable element. The method also includes forming the flexible circuit strips with respective different symbols marked thereon and optionally with respective alignment markings. Each strip generally includes one or more electrodes.

In some embodiments, the method includes forming a flexible circuit panel which comprises the flexible circuit strips in uncut form, and cutting the flexible circuit panel to form the flexible circuit strips as separated strips. In some embodiments, forming the flexible circuit panel includes forming the flexible circuit panel with multiple copies of each of the symbols, for example, multiple strips with letter A thereon, and multiple strips with letter B thereon, and so on.

The method includes attaching one end of each flexible circuit strip to the catheter coupler with the flexible circuit strips being ordered around a circumference of the catheter coupler responsively to the respective symbols of the flexible circuit strips. For example, the flexible circuit strips may be ordered around the catheter coupler according to the letters marked on the strips starting at letter A, followed by letter B, and so on. In some embodiments, the attaching includes aligning the end of each flexible circuit strip to the catheter coupler responsively to the respective alignment markings of the flexible circuit strips.

During testing of the catheter, the method may include aligning a plane of deflection of the distal end assembly with a deflection measurement element responsively to one or more of the symbols of one or more of the flexible circuit strips (e.g., aligning the strips marked A and F with a plane of the deflection measurement element, deflecting the catheter (e.g., to a maximum deflection), and checking a deflection of the catheter with the deflection measurement element. In some embodiments, deflection measurement element may include a laminated paper drawing may be used which shows a nominal curve and an acceptable zone in which the deflectable area may fall.

During other testing of the catheter, the method may include checking a continuity of electrodes of the catheter responsively to the symbols of the flexible circuit strips. For example, the electrodes may be tested for the strip marked with letter A, followed by the strip marked with letter B, and so on.

During a calibration procedure, the method may include aligning the distal end assembly with a position tracking system (e.g., a magnetic position tracking system) responsively to one or more of the symbols of one or more of the flexible circuit strips (e.g., aligning the strip marked A with an axis of a magnetic radiator), and performing a calibration of the catheter with the position tracking system responsively to the aligning.

System Description

Reference is now made to FIG. 1, which is a schematic view of a catheter 10 constructed and operative in accordance with an embodiment of the present invention. The catheter 10 described with reference to FIGS. 1-9 is a basket catheter by way of example. The catheter 10 may be implemented as any suitable spline-based catheter, for example, the PENTARAY® of Biosense Webster of Irvine, California. The catheter 10 described with reference to FIGS. 1-9 includes ten splines. The catheter 10 may be implemented with any suitable number of splines.

The catheter 10 includes an elongated deflectable element 12 having a distal end 14, a coupler 16 connected to the distal end 14, and a pusher 18 including a distal portion 20. The pusher 18 is configured to be advanced and retracted through the deflectable element 12, for example, using a manipulator or handle (not shown). The catheter 10 also includes a distal end assembly 22 comprising a plurality of flexible circuit strips 24 (only some labeled for the sake of simplicity). Each flexible circuit strip 24 includes multiple electrodes 26 disposed thereon (only some labeled for the sake of simplicity). In some embodiments, a strip 24 may include one electrode 26. The coupler 16 is connected to the elongated deflectable element 12. The proximal end of the coupler 16 may be connected to the elongated deflectable element 12 using any suitable connection method, such as using adhesive, for example, epoxy. In some embodiments, the coupler 16 and the elongated deflectable element 12 are formed as an integral element. The catheter 10 also includes a nose connector 30 connected distally to the pusher 18. One end of each flexible circuit strip 24 is connected to the inner surface of the coupler 16 and another end of each flexible circuit strip 24 is connected to the inner surface of the nose connector 30 as described in more detail with reference to FIG. 7. The catheter 10 also includes a nose cap 32 covering the distal end of the nose connector 30. The ends of the flexible circuit strips 24 are folded over into the nose connector 30. In some embodiments, the ends of the flexible circuit strips 24 may not be folded over.

Each flexible circuit strip 24 is backed with an elongated resilient support element 48 (only one labeled for the sake of simplicity) providing a shape of the distal end assembly 22 in the expanded form of the distal end assembly 22. The elongated resilient support elements 48 may include any suitable material, for example, but not limited to, Nitinol and/or Polyetherimide (PEI). The elongated resilient support elements 48 may run from the proximal end of the flexible circuit strips 24 until hinges 28 (only one labeled for the sake of simplicity) described in more detail with reference to FIG. 7. In some embodiments, the elongated resilient support elements 48 are optional.

Figure 2:
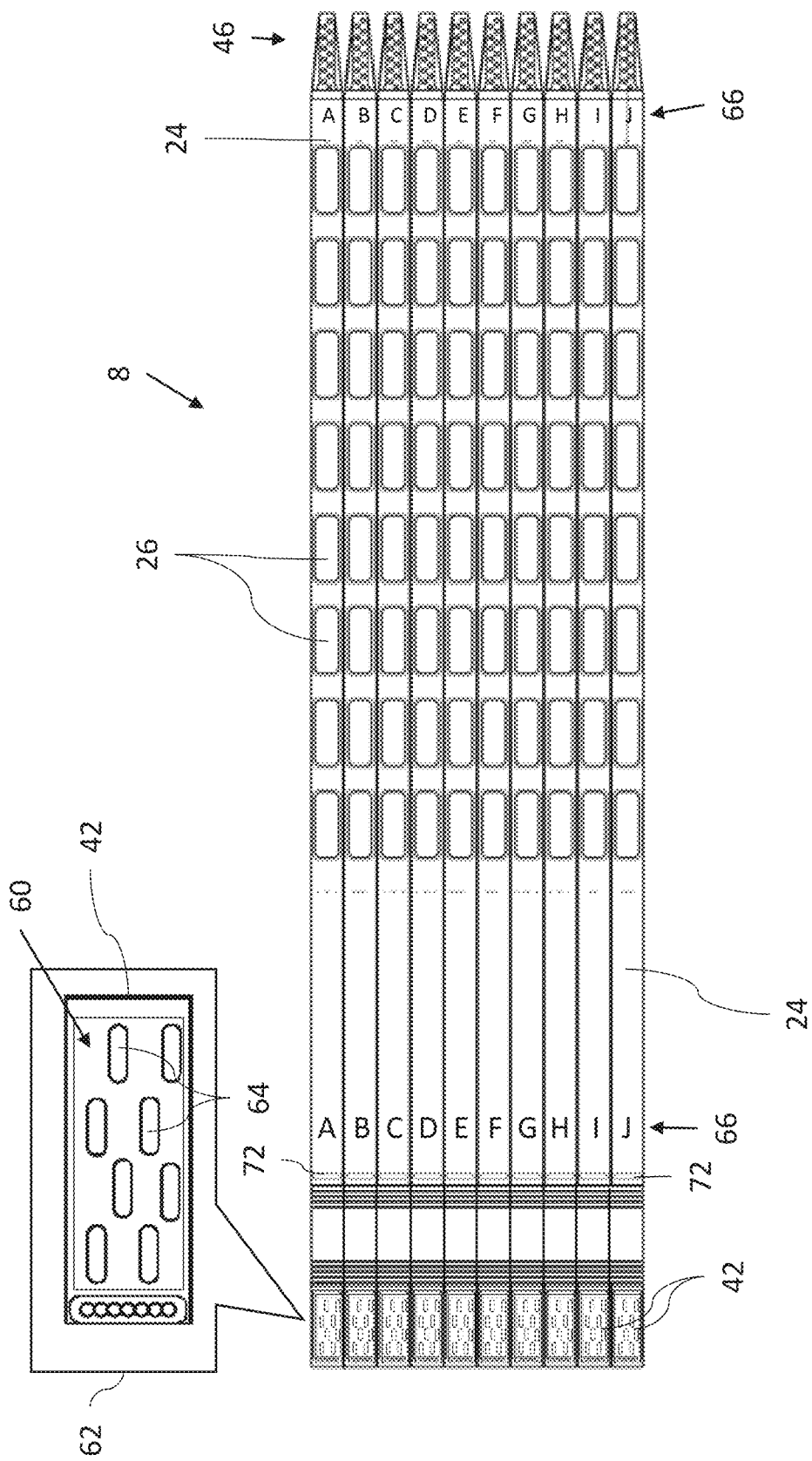
FIG. 2 is a schematic view of a panel of flexible circuits constructed and operative in accordance with an embodiment of the present invention.

Reference is now made to FIG. 2, which is a schematic view of a flexible circuit panel 8 constructed and operative in accordance with an embodiment of the present invention. The flexible circuit strips 24 may be formed from a single piece of polymer, such as polyimide. Circuit strips 24 may be connected to each other by polyimide, or assembled as individual pieces that are held in proper alignment and secured to coupler 16. Respective first ends 42 of the respective flexible circuit strips 24 include an electrical connection array 60. An inset 62 shows that the electrical connection array 60 includes electrical contacts 64 thereon (only some labeled for the sake of simplicity). The electrical contacts 64 are connected via traces (not shown) on the back of the flexible circuit strips 24 to respective ones of the electrodes 26 disposed on the front of the flexible circuit strips 24. Wires (not shown) may connect the electrodes 26 to control circuitry (not shown) via the electrical contacts 64. The wires may be disposed in lumens (not shown) of the elongated deflectable element 12 (FIG. 1).

The flexible circuit strips 24 may have any suitable dimensions. For example, the length of the flexible circuit strips 24 may be in the range of 10 mm to 60 mm, e.g., 30 mm, the width of the flexible circuit strips 24 may be in the range of 0.25 mm to 3 mm, e.g., 0.72 mm, and the thickness of the flexible circuit strips 24 may be in the range of 0.005 mm to 0.14 mm.

Each flexible circuit strip 24 is labeled with a different letter or other symbol 66. In the example of FIG. 2, each strip 24 is labeled with a different letter twice, once close to end 42 and once close to the other (tapered) end 46. For example, a letter A is disposed close to the end 42 of one of the flexible circuit strips 24, and another letter A is disposed close to the other end 46 of that strip 24. Any suitable symbol may be used, for example, numerals, letters of any alphabet or other symbols. The symbols may be added during the circuit manufacturing process through standard lithographic methods such as etching, sputtering, plating, or direct laser marking. Each flexible circuit strips 24 may also include an alignment marking 72 (e.g., a line or other mark or symbol). Only some of the alignment markings 72 are labeled for the sake of simplicity.

Figure 3:
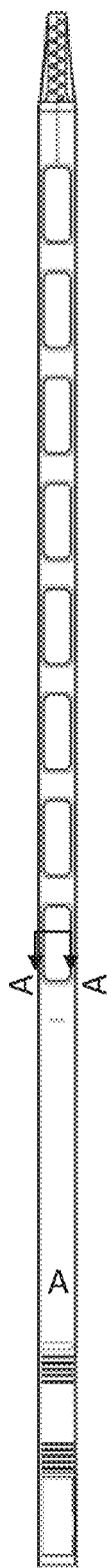
FIG. 3 is a schematic view of a single flexible circuit strip comprised in the panel of FIG. 2.

Reference is now made to FIG. 3, which is a schematic view of a single flexible circuit strip cut 24 from the panel 8 of FIG. 2. The cut flexible circuit strips 24 may then be reinforced using the elongated resilient support elements 48 as well as connected to other elements and coverings as described in more detail with reference to FIG. 4.

Figure 4:
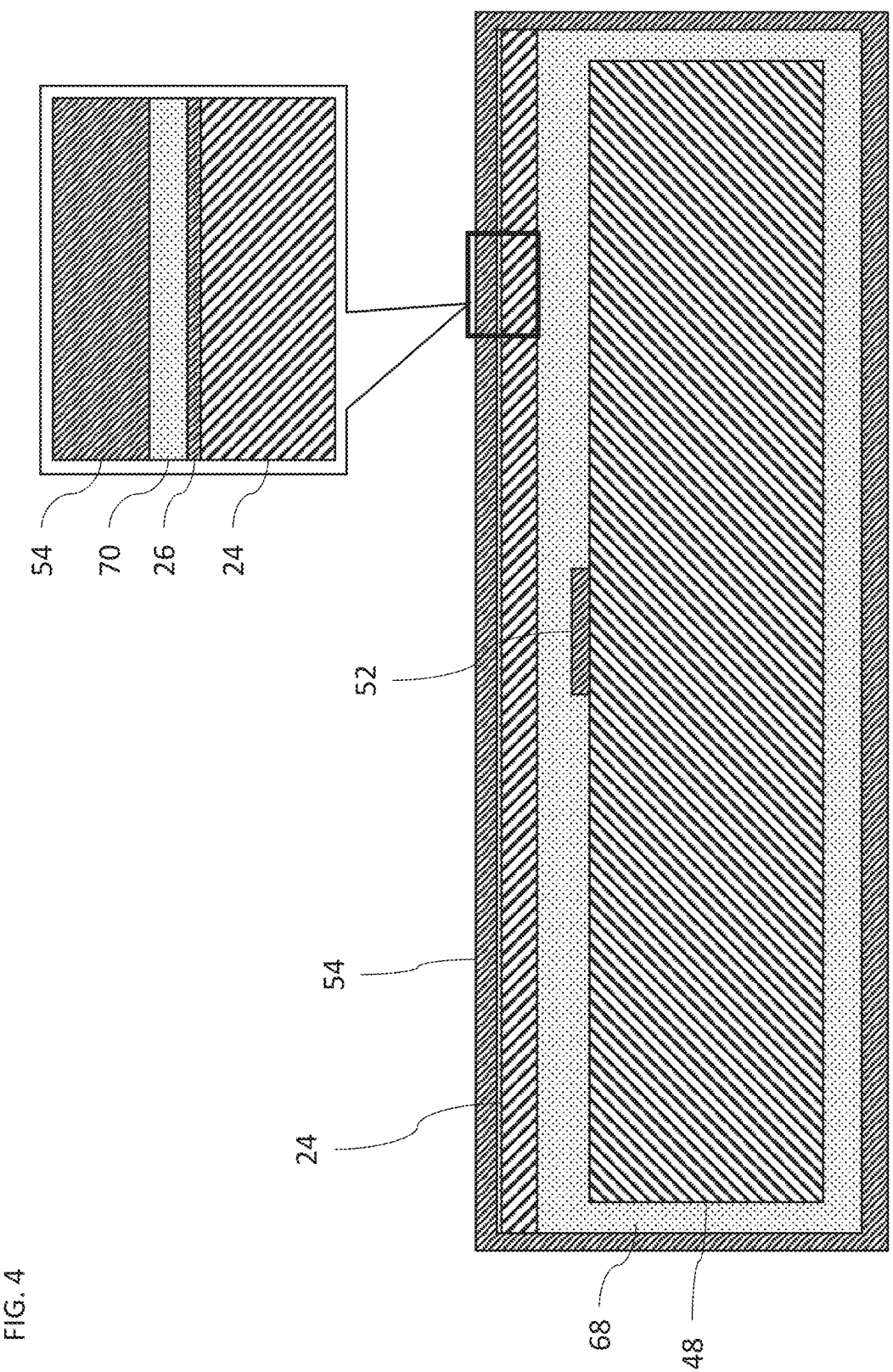
FIG. 4 is a cross-sectional view through line A:A of FIG. 3.

Reference is now made to FIG. 4, which is a cross-sectional view through line A:A of FIG. 3.

A yarn 52 may be run along the length of the elongated resilient support element 48 (FIG. 1), e.g., formed from Nitinol or Polyethylenimine (PEI), and beyond so that the yarn 52 also runs the length of the hinge 28 (FIG. 1). The elongated resilient support elements 48 may have any suitable thickness, for example, in the range of 0.025 mm to 0.25 mm. A covering 68, such as a thermoplastic polymer resin shrink wrap (PET), may be placed over the yarn 52 and the elongated resilient support element 48. Epoxy may be injected into the covering 68. Heat may then be applied to the covering 68 thereby shrinking the covering 68 over the yarn 52 and the elongated resilient support element 48. One reason to cover the elongated resilient support element 48 with the covering 68 is to electrically isolate the elongated resilient support element 48 from the circuit traces of the flexible circuit strip 24. The covering 68 may be omitted, for example, if the elongated resilient support element 48 is covered with an insulating coating (e.g., polyurethane) or is comprised of an insulating material.

The flexible circuit strip 24 may then be placed over the yarn 52 and the elongated resilient support element 48 with the circuit trace side of the flexible circuit strip 24 facing the elongated resilient support element 48 and the electrode(s) 26 of the flexible circuit strips 24 facing away from the elongated resilient support element 48. A covering 54 may then be disposed around the flexible circuit strip 24, yarn 52, and elongated resilient support element 48 combination, and epoxy 70 is injected into the covering 54. The covering 54 may then be heated, thereby shrinking the covering 54 around the combination. The flexible circuit strips 24 are therefore covered with the covering 54, e.g., a thermoplastic polymer resin shrink wrap (PET).

The yarn 52 may comprises any one or more of the following: an ultra-high-molecular-weight polyethylene yarn; or a yarn spun from a liquid-crystal polymer. The yarn 52 may be any suitable linear density, for example, in a range between 25 denier and 250 denier.

Figure 5:
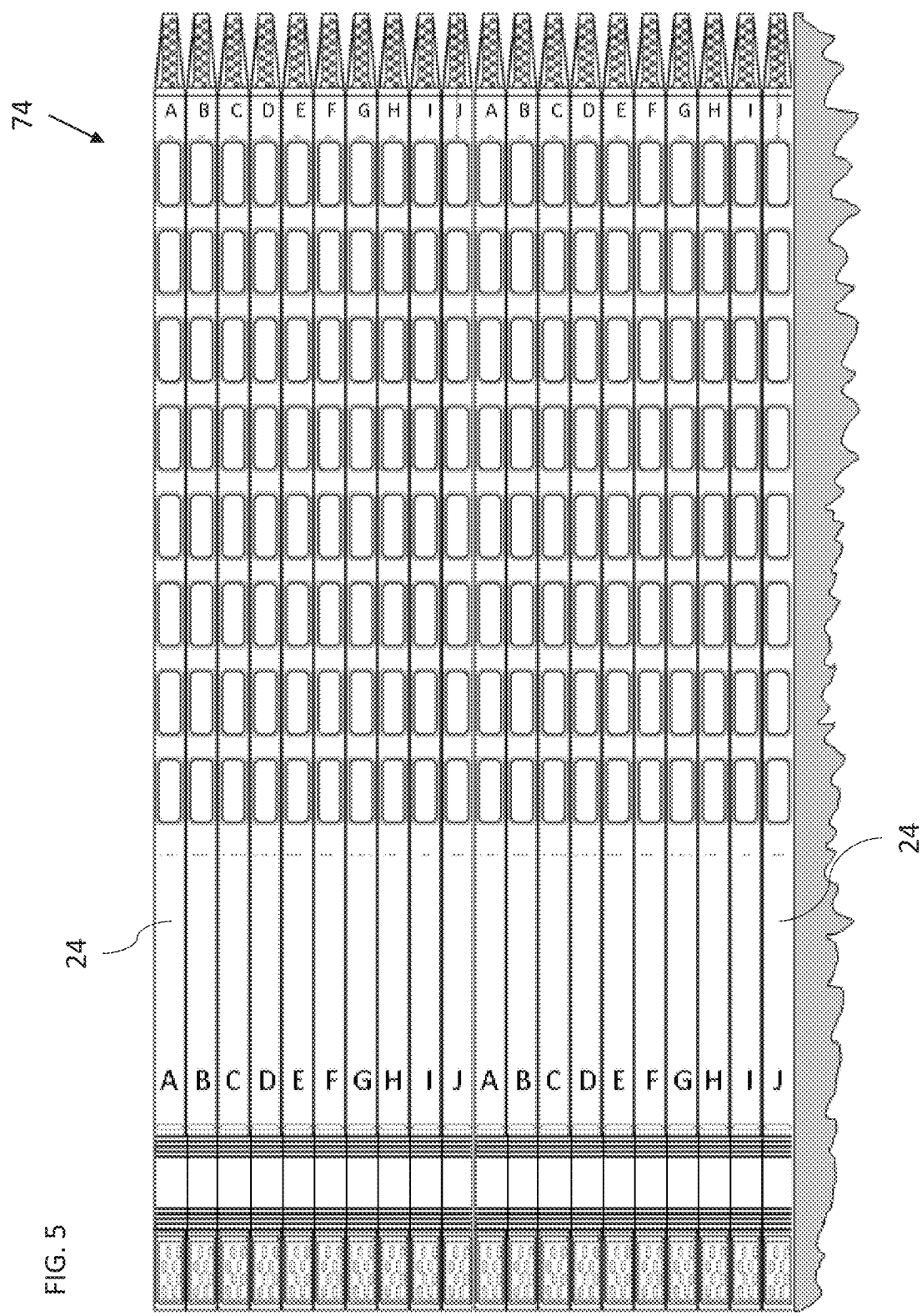
FIG. 5 is a schematic view of a panel of flexible circuits with multiple copies of different symbol strips.

Reference is now made to FIG. 5, which is a schematic view of a flexible circuit panel 74 with multiple copies of different symbol strips 24. The flexible circuit panel 74 provides duplicate flexible circuit strips 24 (only some labeled for the sake of simplicity) on a single panel so that if one strip 24 is faulty, another one with the same symbol may be used instead. For example, 880 circuit strips 24 may be formed on a single flexible circuit panel with the strips 24 being labeled A through J (for example) again and again. The flexible circuit panel is then cut up. If one of the strips 24 marked "A" (for example) proves to be faulty, another "A" strip 24 may be used instead, and so on.

Figure 6:
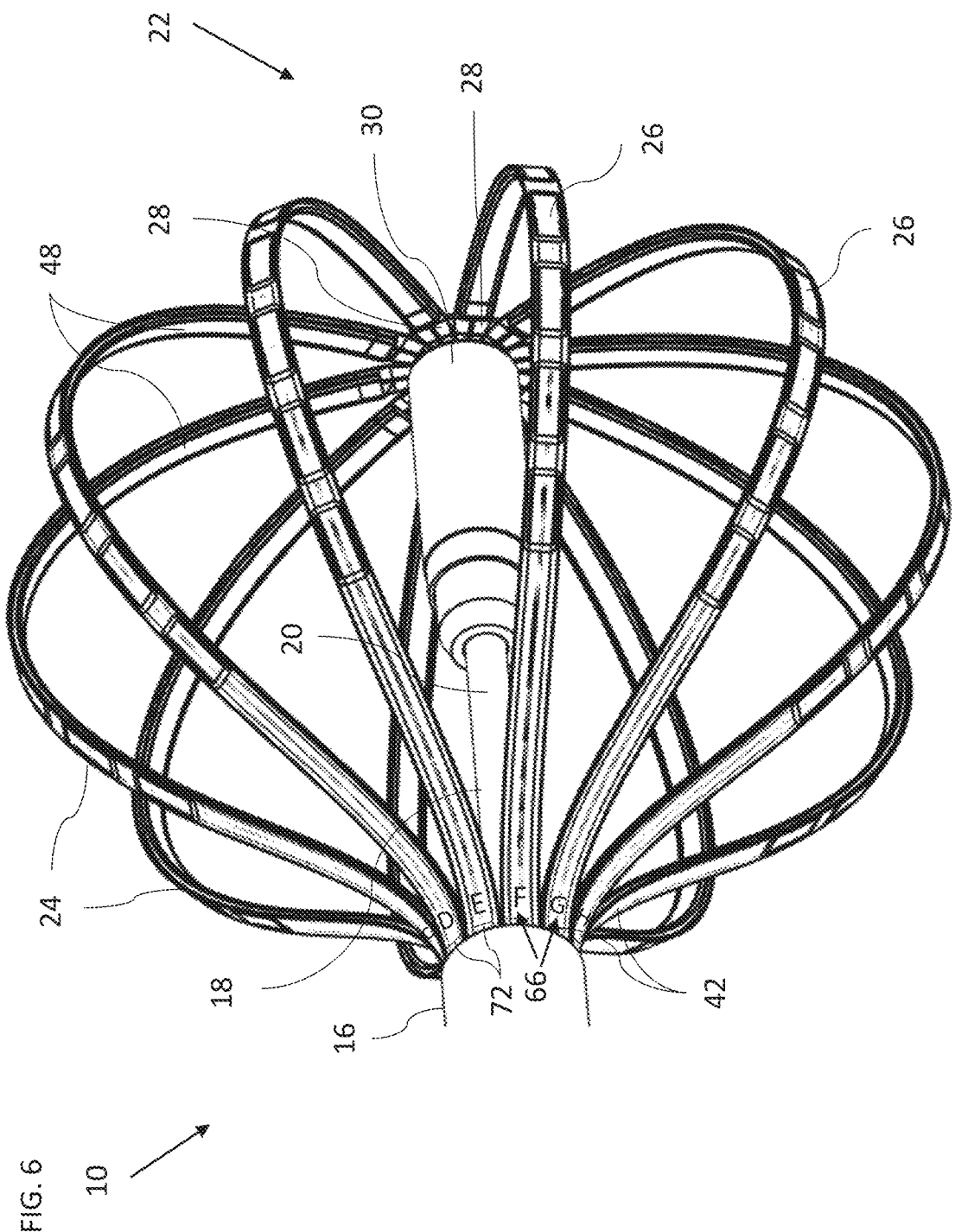
FIGS. 6 and 7 are schematic views of the catheter of FIG. 1 showing the symbols on the flexible circuit strips.
Figure 7:
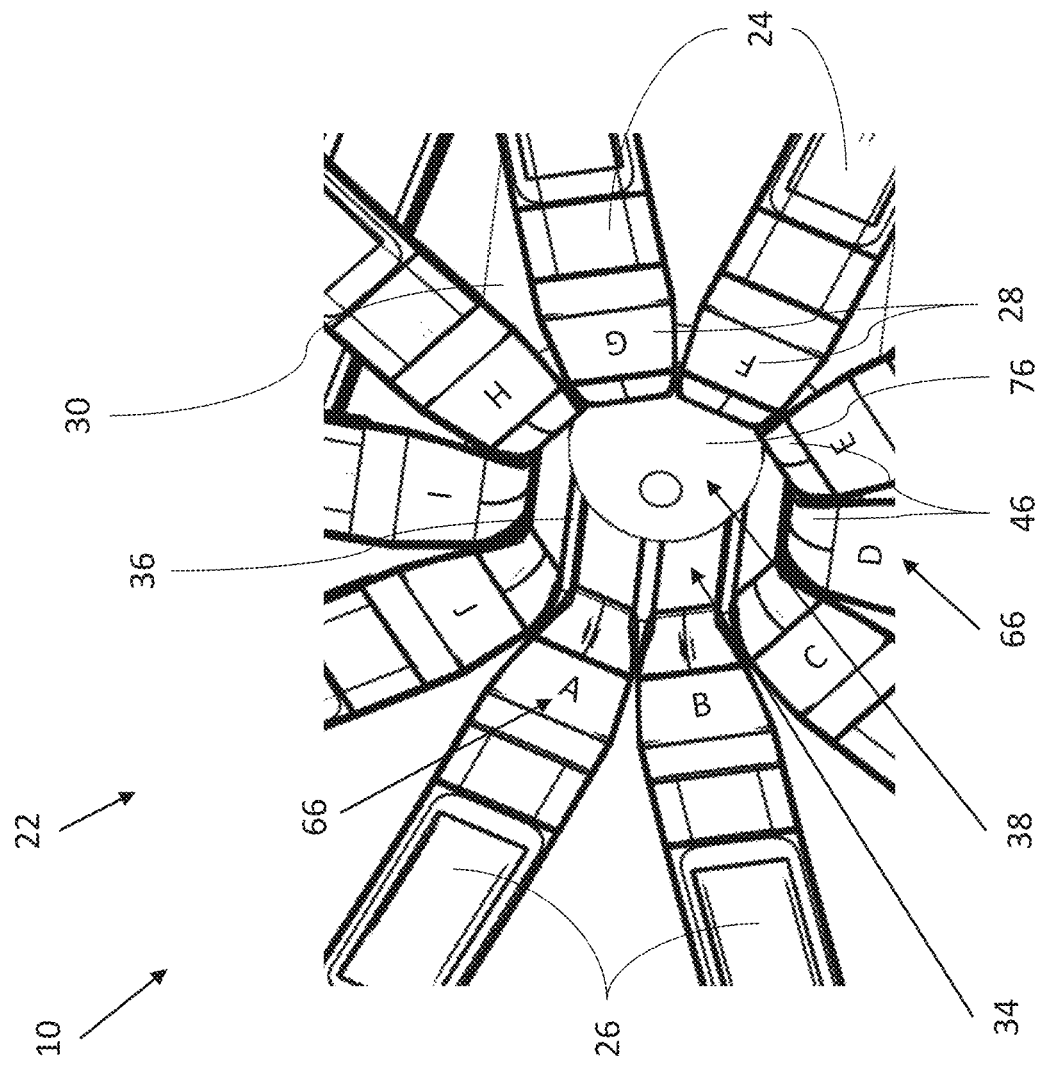

Reference is now made to FIGS. 6 and 7, which are schematic views of the catheter 10 of FIG. 1 showing the symbols 66 on the flexible circuit strips 24.

FIG. 6 shows the nose connector 30 connected to the distal portion 20 of the pusher 18. FIGS. 6 and 7 show that the flexible circuit strips 24 are connected via the hinges 28 (only some labeled for the sake of simplicity) of the flexible circuit strips 24 to the nose connector 30. The flexible circuit strips 24 are disposed circumferentially around the distal portion 20 of the pusher 18, with first ends 42 (FIG. 2) of the strips 24 being connected to an inner surface of the coupler 16.

FIG. 7 shows the nose cap 32 (FIG. 1) removed from the catheter 10 to illustrate how the flexible circuit strips 24 are connected to the nose connector 30. The nose connector 30 includes a distal receptacle 34 having an inner surface 36 and a distal facing opening 38. Second ends 46 (only some labeled for the sake of simplicity) of the strips 24 comprising the respective hinges 28 entering the distal facing opening 38 are connected to the inner surface 36 of the distal receptacle 34 of the nose connector 30.

As previously mentioned with reference to FIG. 1, the elongated resilient support elements 48 extend along inner surface of the respective strips 24 from the coupler 16 until before the respective hinges 28. The hinge region may therefore be much thinner than the region including the elongated resilient support element 48. The hinges 28 may have any suitable thickness, for example, in the range of 10 to 140 microns.

FIG. 7 also shows that the second ends 46 of the respective flexible circuit strips 24 are tapered along the width of the flexible circuit strips 24 to allow inserting the second ends 46 into the distal receptacle 34 without overlap. The hinges 28 may be connected to the inner surface 36 of the distal receptacle 34 using any suitable adhesive, for example, epoxy, and/or using any suitable connection method. As previously mentioned with reference to FIG. 4, the hinges 28 of the flexible circuit strips 24 are supported with a length of yarn 52 (FIG. 4), which typically runs the length of each respective flexible circuit strip 24. FIG. 7 also shows a position sensor 76 disposed in the distal receptacle 34 of the nose connector 30.

FIGS. 6 and 7 show the distal end assembly 22 including the flexible circuit strips 24 with respective different symbol 66 (only some labeled for the sake of simplicity) marked thereon, and each strip 24 including electrode(s) 26 (FIG. 6). The end 42 of each flexible circuit strip 24 is connected to the catheter coupler 16 with the flexible circuit strips 24 being ordered around a circumference of the catheter coupler 16 responsively to the respective symbols 66 of respective flexible circuit strips 24. FIG. 6 also shows the alignment markings 72 (only some labeled for the sake of simplicity) used to align the flexible circuit strips 24 with the distal edge of the coupler 16. When the coupler 16 is transparent or translucent, the alignment markings 72 may be aligned proximally to the distal edge of the coupler 16 (i.e. inside the coupler 16) as the alignment marking 72 may then be seen from outside of the coupler 16.

Figure 8:
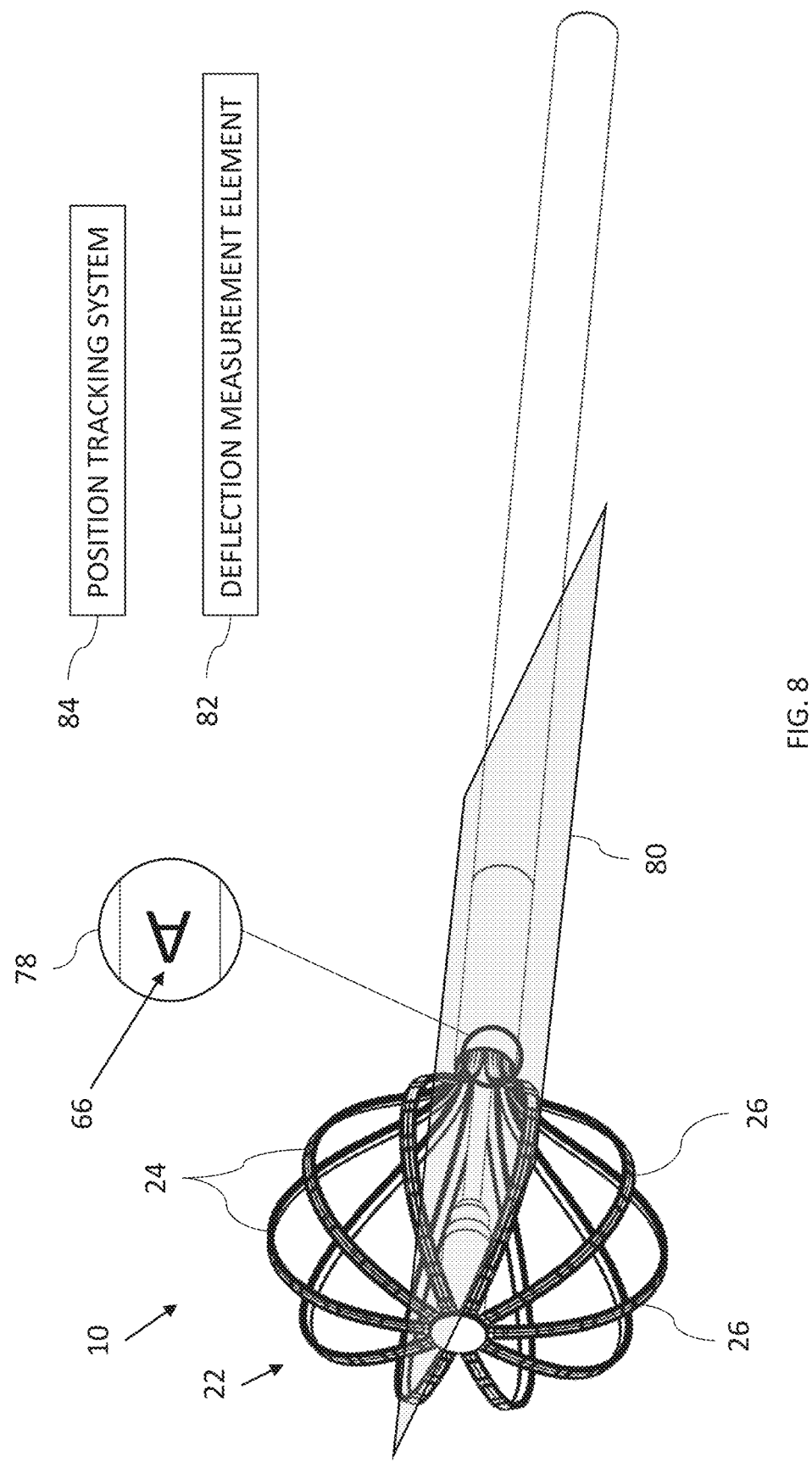
FIG. 8 is a schematic view illustrating configuration and testing of the catheter of FIG. 1.

Reference is now made to FIG. 8, which is a schematic view illustrating configuration and testing of the catheter 10 of FIG. 1. The symbol 66 (e.g., the letter A shown in the inset 78) allows a user to easily align a plane 80 of deflection of the catheter 10 with a deflection measurement element 82, and/or to align the catheter 10 with a position tracking system 84, which may include magnetic radiators aligned in a given configuration, and/or to easily select electrodes 26 (only some labeled) from among the different flexible circuit strips 24 (only some labeled) for testing.

Figure 9:
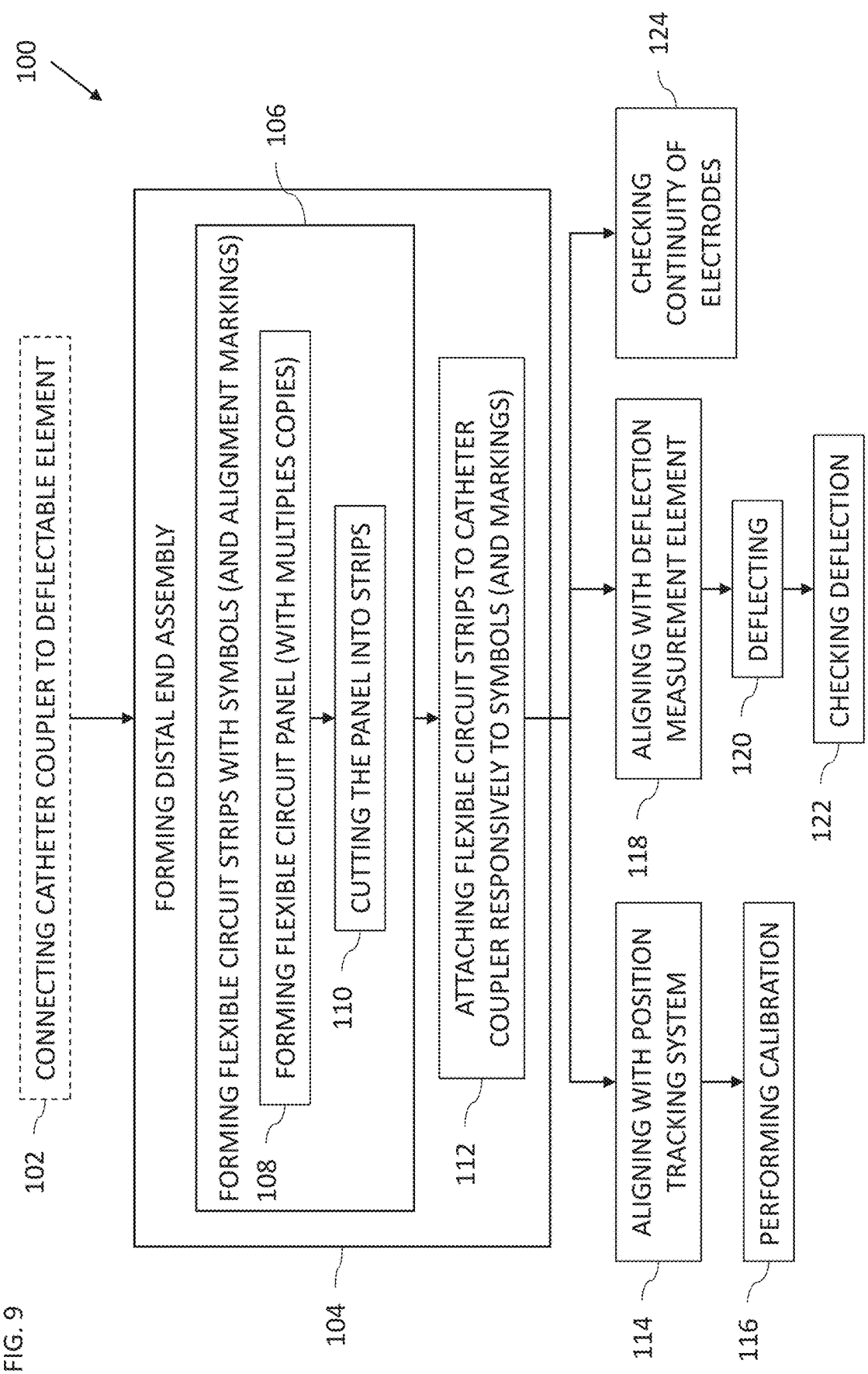
FIG. 9 is a flowchart including steps in a method of manufacture and testing of the catheter of FIG. 1.

Reference is now made to FIG. 9, which is a flowchart 100 including steps in a method of manufacture and testing of the catheter 10 of FIG. 1. Reference is also made to FIG. 1. The method optionally includes connecting (block 102) the coupler 16 to the elongated deflectable element 12. The method includes forming (block 104) the distal end assembly 22. The step of block 104 includes forming (block 106) the flexible circuit strips with respective different symbols 66 (FIG. 2) marked thereon and optionally with respective alignment markings 72 (FIG. 2), each strip including at least one respective electrode 26. The step of block 106 may include forming (block 108) the flexible circuit panel 8 (FIG. 2) comprising the flexible circuit strips 24 in uncut form, and cutting (block 110) the flexible circuit panel 8 to form the flexible circuit strips 24 as separated strips 24. In some embodiments, the step of block 108 includes forming a flexible circuit panel 74 (FIG. 5) with multiple copies of each of the symbols 66. In other words, forming multiple identical flexible circuit strips 24. The step of block 104 also includes attaching (block 112) end 42 (FIG. 2) of each flexible circuit strip 24 to the coupler 16 (and optionally the second end 46 (FIG. 7) of each flexible circuit strip 24 to the nose connector 30 (FIG. 7)) with the flexible circuit strips 24 being ordered around a circumference of the catheter coupler 16 responsively to the respective symbols 66 of respective flexible circuit strips 24. In some embodiments, the attaching includes aligning end 42 of each flexible circuit strip 24 to the catheter coupler 16 responsively to the respective alignment markings 72 of the respective flexible circuit strips 24.

As part of calibrating the catheter 10, the method may include aligning (block 114) the distal end assembly 22 with the position tracking system 84 (FIG. 8) responsively to one or more of the symbols 66 of a respective one or more of the flexible circuit strips 24 (e.g., aligning the strip 24 marked A with an axis of one or more of the magnetic radiators of the position tracking system 84), and performing (block 116) a calibration of the catheter 10 with the position tracking system 84 responsively to the aligning.

As part of a testing procedure, the method may include aligning (block 118) the plane 80 (FIG. 8) of deflection of the distal end assembly 22 with the deflection measurement element 82 (FIG. 8) responsively to one or more of the symbols 66 of a respective one or more of the flexible circuit strips 24, deflecting (block 120) the catheter 10 (e.g., fully deflecting the catheter 10), and checking (block 122) a deflection of the catheter 10 with the deflection measurement element 82. As part of a testing procedure, the method may include checking (block 124) a continuity of electrodes 26 of the catheter 10 responsively to respective ones of the symbols 66 of respective ones of the flexible circuit strips 24.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 72% to 108%.

Various features of the invention which are, for clarity, described in the contexts of separate embodiments may also be provided in combination in a single embodiment. Conversely, various features of the invention which are, for brevity, described in the context of a single embodiment may also be provided separately or in any suitable sub-combination.

The embodiments described above are cited by way of example, and the present invention is not limited by what has been particularly shown and described hereinabove. Rather the scope of the invention includes both combinations and sub-combinations of the various features described hereinabove, as well as variations and modifications thereof which would occur to persons skilled in the art upon reading the foregoing description and which are not disclosed in the prior art.

What is claimed is:

1. A catheter manufacturing method, comprising:
   forming flexible circuit strips with respective different symbols marked thereon, each strip including at least one respective electrode;
   attaching one end of each of the flexible circuit strips to a catheter coupler with the flexible circuit strips being ordered around a circumference of the catheter coupler responsively to the respective symbols of respective ones of the flexible circuit strips;
   forming a distal end assembly of a catheter, the distal end assembly comprising the flexible circuit strips attached to the catheter coupler;
   aligning one of the flexible circuit strips with an axis of a position tracking system; and
   performing a calibration of the catheter with the position tracking system responsively to the aligning.

2. The method according to claim 1, further comprising connecting the catheter coupler to an elongated deflectable element.

3. The method according to claim 1, wherein:
   the forming the flexible strips includes forming the flexible circuit strips with respective alignment markings; and
   the attaching includes aligning the end of each of the flexible circuit strips to the catheter coupler responsively to the respective alignment markings of respective ones of the flexible circuit strips.

4. The method according to claim 1, further comprising:
   forming a flexible circuit panel comprising the flexible circuit strips in uncut form; and cutting the flexible circuit panel to form the flexible circuit strips as separated strips.

5. The method according to claim 4, wherein forming the flexible circuit panel includes forming the flexible circuit panel with multiple copies of each of the symbols.

6. The method according to claim 1, further comprising:
aligning the distal end assembly with a deflection measurement element;
deflecting the catheter; and
checking a deflection of the catheter with the deflection measurement element.

7. The method according to claim 1, further comprising checking a continuity of each electrode of the electrodes of the catheter in an ascending order, the ascending order corresponding to respective ones of the symbols of respective ones of the flexible circuit strips.

8. The method of claim 3, wherein the respective alignment markings are visible from outside the catheter coupler.

9. The method according to claim 5, wherein each flexible circuit strip comprises a first copy of a respective symbol at a first end of the flexible circuit strip and a second copy of the respective symbol at a second end of the flexible circuit strip.

10. The method according to claim 1, where the aligning the one of the flexible circuit strips with the axis of the position tracking system further comprises aligning the one of the flexible circuit strips with a magnetic radiator of the position tracking system.

11. The method according to claim 1, wherein the symbols of the flexible circuit strips comprise alphanumeric characters.

12. The method according to claim 11, wherein the symbols are ordered in an ascending order around the circumference of the catheter.

13. The method according to claim 1, wherein each of the flexible circuit strips comprises a connection array disposed on a first end of each flexible circuit strip.

14. The method according to claim 13, wherein the connection array of each flexible circuit strip comprises at least one electrical contact.

15. The method according to claim 14, wherein at least one electrical contact is connected to the at least one respective electrode via at least one trace, wherein the at least one trace is disposed on a back of the flexible circuit strip.

* * * * *